United States Patent [19]

Oronsky

[11] Patent Number: 4,496,549
[45] Date of Patent: Jan. 29, 1985

[54] TREATMENT OF MALARIA WITH ANTIBIOTICS

[75] Inventor: Arnold L. Oronsky, Chappaqua, N.Y.

[73] Assignee: American Cyanamid Company, Stamford, Conn.

[21] Appl. No.: 458,242

[22] Filed: Jan. 17, 1983

[51] Int. Cl.$^3$ .................... A61K 31/70; A61K 31/71; A61K 31/35
[52] U.S. Cl. ........................................................ 514/27
[58] Field of Search ................................ 424/283, 181

[56] References Cited

U.S. PATENT DOCUMENTS 4,278,663  7/1981  Liv et al. .............................. 424/180
4,407,946 10/1983  Labeda et al. ....................... 435/170

Primary Examiner—Jerome D. Goldberg
Assistant Examiner—Joyce L. Morrison
Attorney, Agent, or Firm—M.-E. M. Timbers; J. W. Richards

[57] ABSTRACT

This invention relates to a novel method for the treatment of malarial infections in warm-blooded animals using the antibiotics X-14868A, LL-C23024 beta, LL-C23024 iota, and combinations theory and to compositions containing these antibiotics.

2 Claims, No Drawings

TREATMENT OF MALARIA WITH ANTIBIOTICS

BACKGROUND OF THE INVENTION

Antibiotic X-14868A is the subject of U.S. Pat. No. 4,278,663, assigned to Hoffman-La Roche, and is disclosed as being useful in the field of veterinary medicine for the treatment of coccidiosis, prevention and treatment of ketosis, improvement of feed utilization, and treatment and prevention of swine dysentery, as well as being useful as a bacteriocidal antiseptic.

U.S. patent application Ser. No. 116,696, now U.S. Pat. No. 4,278,663, discloses antibiotic X-1468A as having the structure:

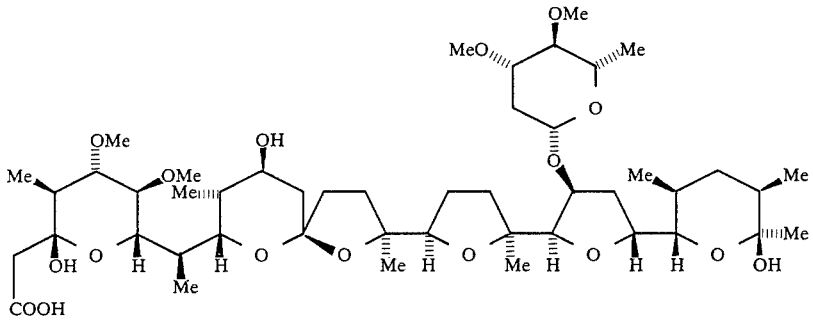

This antibiotic is described in U.S. Pat. No. 4,278,663 as being produced by the aerobic fermentation of a new species of Nocardia, designated Nocardia sp. X-14868, ATCC 31585.

A culture of the living organism, with the laboratory desigation X-14868, has been deposited in the American Type Culture Collection, Rockville, Md. and added to its permanent collection of microorganism as ATCC 31585. The culture has been identified as a strain of Nocardia. The new microorganism was isolated from a soil sample collected from beach sand in Colloroy, Australia. A representative strain of Nocardia sp. X-14868 and the antibiotic itself have the characteristics disclosed in the '663 patent incorporated herein by reference thereto.

Antibiotic X-14868A is also the subject of U.S. Pat. No. 4,407,946, assigned to American Cyanamid Company, which describes a process for producing said antibiotic employing aerobic fermentation of the novel microorganism *Actinomadura yumaense.*

A representative strain of this novel microorganism was isolated from a soil sample collected in Yuma County, Ariz. and is maintained in the culture collection of the Lederle Laboratories Division, American Cyanamid Company, Pearl River, N.Y. as Culture Number LL-C23024. A viable culture of this representative strain has been deposited with the Culture Collection Laboratory, Northern Regional Center, U.S. Department of Agriculture, Peoria, Ill. 61604, and has been added to its permanent collection under the Accession Number NRRL 12515. A representative strain and the antibiotic itself have the characteristics disclosed in U.S. Pat. No. 4,407,946 incorporated herein by reference thereto.

The antibiotic LL-C23024 beta (X-14868C) is the subject of application for U.S. Letters Patent, Ser. No. 372,784, filed Apr. 28, 1982, assigned to American Cyanamid Company, now abandoned which discloses said antibiotic in terms of its physical and chemical characteristics as well as methods for its production by aerobic fermentation of strains of the microorganism *Actinomadura yumaense* (including NRRL 12515) and establishes its utility in terms of its activity against gram-positive bacteria and as an anticoccidial agent.

Application Ser. No. 372,784 discloses antibiotic LL-C23024 beta as having the structure:

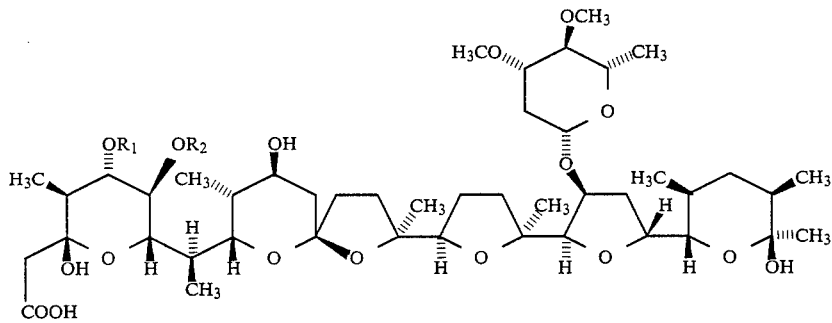

wherein $R_1$ and $R_2$ are different and are each selected from the group consisting of H and $CH_3$.

Antibiotic LL-C23024 beta also is formed during the cultivation under controlled conditions of *Actinomadura yumaense* sp. nov. (NRRL 12515). The characteristics of antibiotic LL-C23024 beta as disclosed in application Ser. No. 372,784 are incorporated herein by reference thereto.

The antibiotic LL-C23024 iota (X-14868B) is the subject of application for Letters Patent Ser. No. 379,224, filed May 17, 1982, assigned to American Cyanamid Company, now abandoned, which discloses said antibiotic in terms of its chemical and physical characteristics as well as methods for its production by aerobic fermentation of strains of the microorganism *Actinomadura yumaense* (including NRRL 12515) and establishes its utility in terms of its activity against gram-positive bacteria and as an anticoccidial agent.

Antibiotic LL-C23024 iota appears to have four methoxy groups, the same sugar observed in antibiotic X-14868A, and one carboxyl group.

Antibiotic LL-C23024 iota is formed during the cultivation under controlled conditions of *Actinomadura yumaense* sp. nov. (NRRL 12515). The characteristics of antibiotic LL-C23024 iota as disclosed in application Ser. No. 379,224 are incorporated herein by reference thereto.

BRIEF SUMMARY OF THE INVENTION

It has now been discovered that antibiotics X-14868A, LL-C23024 beta, and LL-C23024 iota are active as antimalarial agents.

This invention is concerned with a method of controlling malaria in warm-blooded animals, comprising administering to said animals an antimalarial effective amount of an antibiotic selected from the group consisting of X-14868A, LL-C23024 beta, and LL-C23024 iota, as well as said method in association with a pharmaceutically acceptable carrier.

This invention is also concerned with a therapeutic composition having antimalarial activity in warm-blooded animals containing an antimalarial effective amount of an antibiotic selected from the group consisting of X-14868A, LL-C23024 beta, and LL-C23024 iota and a pharmaceutically acceptable carrier.

This invention is further concerned with a method for the preparation of a therapeutic composition having antimalarial activity in warm-blooded animals, characterized by admixing an antibiotic selected from the group consisting of X-14868A, LL-C23024 beta, and LL-C23024 iota, with a pharmaceutically acceptable carrier.

DETAILED DESCRIPTION OF THE INVENTION

The utility of the present invention was established in a test in which human red blood cells were infected with the malarial parasite *Plasmodium falciparum*. Twenty-four hours after infection 0.5%–2.0% of the red blood cells were infected. During the next 3–4 days, parasites continued to grow and infect up to 10–12% of control cells. No further infection continued, and the parasites were totally intracellular.

Twenty-four hours after infection, the test compounds were administered at the indicated concentrations, and four days later the percentage of inhibition of parasite infection was measured. The results appear in the following table, where they are expressed as percent inhibition (i.e., 100% inhibition means no increase in infected cells beyond initial infection) and compared with two known antimalarial agents.

| COMPOUND | CONCENTRATION (MOLAR) | % INHIBITION |
| --- | --- | --- |
| X-14868A | $10^{-7}$ | 100 |
| LL-C23024 beta | $10^{-7}$ | 100 |
| LL-C23024 iota | $10^{-8}$ | 100 |
|  | $10^{-9}$ | 10 |
| Chloroquine | $10^{-7}$ | 100 |
| Mefloquine | $5 \times 10^{-6}$ | 100 |
|  | $10^{-7}$ | 10 |

Since the antibiotics of the present invention contain organic carboxylic groups, they are capable of forming salts with non-toxic pharmaceutically acceptable cations. Thus, salts formed by admixture of the antibiotic free acid with stoichiometric amounts of cations may be formed with cations such as sodium, potassium, calcium, magnesium, and ammonium, as well as organic amine cations such as tri(lower alkyl)amines (e.g., triethylamine, triethanolamine), procaine, and the like. For the purposes of this invention, the antibiotic free acid is equivalent to its pharmaceutically acceptable non-toxic salts, and the use of the salts is contemplated as being within the scope of this invention.

The antibiotics of the present invention may be administered orally or parenterally, e.g., intravenously or intramuscularly. They may be administered by the oral route before or after meals. For suppressive therapy, 500 mg. of the antibiotic may be given once per week. In the therapy of an acute attack of *vivax* or *falciparum* malaria, an initial priming dose of 1 Gm. may be followed by 500 mg. after 6 to 8 hours; then a single dose of 500 mg. may be given on each of three consecutive days. This treatment schedule is suggested to cure *falciparum* malaria. For *vivax* infection, the treatment of the acute attack may be followed by suppressive therapy (500 mg. weekly). The conventional course of the antibiotics in extraintestinal amebiasis in adults may be 1 Gm. daily for 2 days, followed by 500 mg. daily for 2 to 3 weeks. A suggested dose is antimalarial—suppressive, 500 mg. weekly; therapeutic, 1 Gm. immediately, then 500 mg. in 6 hours and 500 mg. on the 2nd and 3rd days; anti-amebic, 500 mg. 3 times a day for 2 weeks, then 700 mg. twice weekly for several months. The optimum dose, of course, varies with the condition and the animal.

The antibiotics of the present invention may be orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 10 and 10,000 milligrams of antibiotic per dosage unit.

The tablets, troches, pills, capsules, and the like may also contain the following: a binder such as gum tragacanth, acacia, corn starch, or gelatin; an excipient such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills, or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

In addition, the active ingredients may be incorporated into sustained release preparations. Preparations of this type would contain greater quantities of the active ingredients.

The antibiotics of the present invention may be used alone or in combination with each other or with one or more other antimalarials or drugs. Such combinations include, for example, X-14868A and LL-C23024 beta; LL-C23024 beta; and LL-C23024 iota; X-14868A, LL-C23024 beta, and LL-C23024 iota; X-14868A and chloroquine; X-14868A and mefloquine; X-14868A and primaquine; X-14868A and quinine; LL-C23024 beta and chloroquine; LL-C23024 beta and mefloquine; LL-C23024 beta and primaquine; LL-C23024 beta and quinine; LL-C23024 iota and chloroquine; LL-C23024 iota and mefloquine; LL-C23024 iota and primaquine; LL-C23024 iota and quinine. Other combinations include, for example, X-14868A, LL-C23024 beta and LL-C23024 iota in combination with one or more of the following: totaquine; quinacrine; sontoquine; chloroquanide; pamaquine; isopentoquine; mepacrine; amodiaquin; proguanil; clociguanil; pyrimethamine; trimethoprim; dapsone; sulfadiazine; sulfadoxine; sulfalene; menactone; tetracycline; and chlortetracycline.

I claim:

1. A method of treating malaria in warm-blooded animals comprising administering to a warm-blooded animal in need of said treatment an anti-malarial effective amount of a compound selected from the group consisting of X-14868A, LL-C23024 beta and LL-C23024 iota.

2. The method in accordance with claim 1 wherein the anti-malarial effective amount administered is about 10 mg to about 1000 mg.

* * * * *